United States Patent
Bandy et al.

(10) Patent No.: US 9,192,353 B2
(45) Date of Patent: Nov. 24, 2015

(54) DATA TRANSMISSION VIA WIDE BAND ACOUSTIC CHANNELS

(75) Inventors: William R. Bandy, Gambrills, MD (US); Yuri Okunev, Middle Island, NY (US); Wayne E. Shanks, Baltimore, MD (US)

(73) Assignee: INNURVATION, INC., Gambrills, MD (US)

( * ) Notice: Subject to any disclaimer, the term of this patent is extended or adjusted under 35 U.S.C. 154(b) by 415 days.

(21) Appl. No.: 12/913,506

(22) Filed: Oct. 27, 2010

(65) Prior Publication Data

US 2011/0237951 A1    Sep. 29, 2011

Related U.S. Application Data (60) Provisional application No. 61/255,354, filed on Oct. 27, 2009.

(51) Int. Cl.
| | |
|---|---|
| *H04B 11/00* | (2006.01) |
| *G01S 1/72* | (2006.01) |
| *A61B 8/12* | (2006.01) |
| *A61B 5/00* | (2006.01) |

(52) U.S. Cl.
CPC ............ *A61B 8/12* (2013.01); *A61B 5/6861* (2013.01); *G01S 1/72* (2013.01); *H04B 11/00* (2013.01)

(58) Field of Classification Search
USPC ............................. 367/134, 137, 138; 600/459
See application file for complete search history.

(56) References Cited

U.S. PATENT DOCUMENTS

| | | | |
|---|---|---|---|
| 3,872,330 A | * 3/1975 | Miller et al. | ............ 310/316.03 |
| 4,987,897 A | 1/1991 | Funke | |
| 5,251,326 A | 10/1993 | Silverman | |
| 5,265,603 A | 11/1993 | Hudrlik | |
| 5,267,033 A | 11/1993 | Hoshino | |
| 5,279,607 A | 1/1994 | Schentag et al. | |
| 5,329,498 A | 7/1994 | Greenstein | |
| 5,395,366 A | 3/1995 | D'Andrea et al. | |
| 5,522,865 A | 6/1996 | Schulman et al. | |
| 5,559,757 A | 9/1996 | Catipovic et al. | |
| 5,604,531 A | 2/1997 | Iddan et al. | |
| 5,741,311 A | 4/1998 | Mc Venes et al. | |
| 5,744,898 A | 4/1998 | Smith et al. | |
| 5,796,827 A | 8/1998 | Coppersmith et al. | |
| 5,833,603 A | 11/1998 | Kovacs et al. | |
| 5,984,875 A | 11/1999 | Brune | |
| 6,023,977 A | * 2/2000 | Langdon et al. | ................ 73/629 |
| 6,076,016 A | 6/2000 | Feierbach | |
| 6,104,913 A | 8/2000 | McAllister | |
| 6,115,636 A | 9/2000 | Ryan | |

(Continued)

FOREIGN PATENT DOCUMENTS

| | | |
|---|---|---|
| EP | 1 492 352 A2 | 12/2004 |
| EP | 1 654 983 A1 | 5/2006 |

(Continued)

*Primary Examiner* — James Hulka
(74) *Attorney, Agent, or Firm* — Sterne, Kessler, Goldstein & Fox P.L.L.C.

(57) ABSTRACT

Embodiments of the present invention relate to ultrasound (acoustic) data transmission systems, in particular data transmission over wide-band acoustic channels with frequency-dependant multi-path propagation. More specifically, embodiments of the invention involve increasing the bit rate in the acoustic channel by means of utilization of the entire ultrasound spectrum available for data transmission inside a human body.

18 Claims, 8 Drawing Sheets

(56) References Cited

U.S. PATENT DOCUMENTS

| | | | |
|---|---|---|---|
| 6,138,513 A * | 10/2000 | Barabash et al. | 73/602 |
| 6,198,965 B1 | 3/2001 | Penner et al. | |
| 6,211,799 B1 | 4/2001 | Post et al. | |
| 6,239,724 B1 | 5/2001 | Doron et al. | |
| 6,240,312 B1 | 5/2001 | Alfano et al. | |
| 6,380,858 B1 | 4/2002 | Yarin et al. | |
| 6,431,175 B1 | 8/2002 | Penner et al. | |
| 6,486,588 B2 | 11/2002 | Doron et al. | |
| 6,504,286 B1 | 1/2003 | Porat et al. | |
| 6,584,348 B2 | 6/2003 | Glukhovsky | |
| 6,597,320 B2 | 7/2003 | Maeda et al. | |
| 6,628,989 B1 | 9/2003 | Penner et al. | |
| 6,702,755 B1 | 3/2004 | Stasz et al. | |
| 6,720,709 B2 | 4/2004 | Porat et al. | |
| 6,754,472 B1 | 6/2004 | Williams et al. | |
| 6,764,446 B2 | 7/2004 | Wolinsky et al. | |
| 6,845,190 B1 | 1/2005 | Smithwick et al. | |
| 6,847,844 B2 | 1/2005 | Sun et al. | |
| 6,867,753 B2 | 3/2005 | Chinthammit et al. | |
| 6,904,308 B2 | 6/2005 | Frisch et al. | |
| 6,934,573 B1 | 8/2005 | Glukhovsky et al. | |
| 6,936,003 B2 | 8/2005 | Iddan | |
| 6,939,292 B2 | 9/2005 | Mizuno | |
| 6,944,316 B2 | 9/2005 | Glukhovsky et al. | |
| 6,950,690 B1 | 9/2005 | Meron et al. | |
| 6,984,205 B2 | 1/2006 | Gazdzinski | |
| 7,009,634 B2 | 3/2006 | Iddan et al. | |
| 7,024,248 B2 | 4/2006 | Penner et al. | |
| 7,039,453 B2 | 5/2006 | Mullick et al. | |
| 7,109,859 B2 | 9/2006 | Peeters | |
| 7,118,529 B2 | 10/2006 | Glukhovsky et al. | |
| 7,118,531 B2 | 10/2006 | Krill | |
| 7,160,258 B2 | 1/2007 | Imran et al. | |
| 7,161,164 B2 | 1/2007 | Glukhovsky | |
| 7,195,588 B2 | 3/2007 | Homan et al. | |
| 7,200,253 B2 | 4/2007 | Glukhovsky et al. | |
| 7,295,226 B1 | 11/2007 | Meron et al. | |
| 7,307,544 B2 | 12/2007 | Kim et al. | |
| 7,336,833 B2 | 2/2008 | Horn | |
| 7,354,397 B2 | 4/2008 | Fujita et al. | |
| 2001/0035902 A1 | 11/2001 | Iddan et al. | |
| 2002/0045830 A1 * | 4/2002 | Powers et al. | 600/459 |
| 2002/0138009 A1 | 9/2002 | Brockway et al. | |
| 2002/0165592 A1 | 11/2002 | Glukhovsky et al. | |
| 2002/0173718 A1 | 11/2002 | Frisch et al. | |
| 2002/0177779 A1 | 11/2002 | Adler et al. | |
| 2003/0013370 A1 | 1/2003 | Glukhovsky | |
| 2003/0043263 A1 | 3/2003 | Glukhovsky et al. | |
| 2003/0045790 A1 | 3/2003 | Lewkowicz et al. | |
| 2003/0069500 A1 * | 4/2003 | Bullis | 600/437 |
| 2003/0114742 A1 | 6/2003 | Lewkowicz et al. | |
| 2003/0139661 A1 | 7/2003 | Kimchy et al. | |
| 2003/0195415 A1 | 10/2003 | Iddan | |
| 2004/0032187 A1 | 2/2004 | Penner et al. | |
| 2004/0114856 A1 | 6/2004 | Kubby et al. | |
| 2004/0122315 A1 | 6/2004 | Krill | |
| 2004/0199222 A1 | 10/2004 | Sun et al. | |
| 2004/0202339 A1 | 10/2004 | O'Brien, Jr. et al. | |
| 2004/0204744 A1 | 10/2004 | Penner et al. | |
| 2004/0236182 A1 | 11/2004 | Iddan et al. | |
| 2004/0258328 A1 | 12/2004 | Adler | |
| 2005/0025368 A1 | 2/2005 | Glukhovsky | |
| 2005/0075555 A1 | 4/2005 | Glukhovsky et al. | |
| 2005/0088299 A1 | 4/2005 | Bandy et al. | |
| 2005/0110881 A1 | 5/2005 | Glukhovsky et al. | |
| 2005/0131302 A1 * | 6/2005 | Poland | 600/459 |
| 2005/0143644 A1 | 6/2005 | Gilad et al. | |
| 2005/0148816 A1 | 7/2005 | Glukhovsky et al. | |
| 2005/0159643 A1 | 7/2005 | Zinaty et al. | |
| 2005/0159789 A1 | 7/2005 | Brockway et al. | |
| 2005/0187433 A1 | 8/2005 | Horn et al. | |
| 2005/0220311 A1 * | 10/2005 | Sun et al. | 381/77 |
| 2005/0222490 A1 | 10/2005 | Glukhovsky et al. | |
| 2005/0228259 A1 | 10/2005 | Glukhovsky et al. | |
| 2005/0249037 A1 * | 11/2005 | Kohn et al. | 367/117 |
| 2005/0272974 A1 | 12/2005 | Iddan | |
| 2005/0281446 A1 | 12/2005 | Glukhovsky et al. | |
| 2006/0004256 A1 | 1/2006 | Gilad et al. | |
| 2006/0009818 A1 | 1/2006 | Von Arx et al. | |
| 2006/0045118 A1 | 3/2006 | Hyoung et al. | |
| 2006/0074275 A1 | 4/2006 | Davidson et al. | |
| 2006/0082648 A1 | 4/2006 | Iddan et al. | |
| 2006/0092908 A1 | 5/2006 | Sung et al. | |
| 2006/0116584 A1 | 6/2006 | Sudol et al. | |
| 2006/0132599 A1 | 6/2006 | Iddan et al. | |
| 2006/0147037 A1 | 7/2006 | Boschetti | |
| 2006/0155174 A1 | 7/2006 | Glukhovsky et al. | |
| 2006/0158512 A1 | 7/2006 | Iddan et al. | |
| 2006/0184039 A1 | 8/2006 | Avni et al. | |
| 2006/0192889 A1 | 8/2006 | Iddan et al. | |
| 2006/0252371 A1 | 11/2006 | Yanagida | |
| 2007/0002604 A1 | 1/2007 | Lin et al. | |
| 2007/0043310 A1 | 2/2007 | Trandafir et al. | |
| 2007/0060979 A1 | 3/2007 | Strother et al. | |
| 2007/0123772 A1 | 5/2007 | Euliano et al. | |
| 2007/0213659 A1 | 9/2007 | Trovato et al. | |
| 2007/0282156 A1 | 12/2007 | Konings | |
| 2008/0045838 A1 * | 2/2008 | Hyuga | 600/463 |
| 2008/0125660 A1 * | 5/2008 | Yao et al. | 600/459 |
| 2008/0213355 A1 | 9/2008 | Bohmer | |
| 2009/0043209 A1 * | 2/2009 | Hirama | 600/459 |

FOREIGN PATENT DOCUMENTS

| | | |
|---|---|---|
| EP | 1 676 522 A1 | 7/2006 |
| EP | 1 693 000 A2 | 8/2006 |
| EP | 1 698 278 A1 | 9/2006 |
| EP | 1 704 812 A1 | 9/2006 |
| EP | 1 737 124 A2 | 12/2006 |
| GB | 2 414 408 A | 11/2005 |
| WO | WO 02/055126 A2 | 7/2002 |
| WO | WO 02/080753 A2 | 10/2002 |
| WO | WO 02/089913 A2 | 11/2002 |
| WO | WO 03/010967 A1 | 2/2003 |
| WO | WO 03/028224 A2 | 4/2003 |
| WO | WO 03/053241 A2 | 7/2003 |
| WO | WO 2004/052209 A1 | 6/2004 |
| WO | WO 2004/054430 A2 | 7/2004 |
| WO | WO 2004/058041 A2 | 7/2004 |
| WO | WO 2005/062715 A2 | 7/2005 |
| WO | WO 2006/034125 A2 | 3/2006 |
| WO | WO 2006/059331 A2 | 6/2006 |
| WO | WO 2006/103665 A2 | 10/2006 |
| WO | WO 2006/114649 A1 | 11/2006 |
| WO | WO 2007/028035 A3 | 3/2007 |
| WO | WO 2007/126247 A1 | 11/2007 |
| WO | WO 2007/143200 A2 | 12/2007 |
| WO | WO 2008/014432 A2 | 1/2008 |
| WO | WO 2008/016194 A2 | 2/2008 |

* cited by examiner

DATA TRANSMISSION VIA WIDE BAND ACOUSTIC CHANNELS

CROSS REFERENCE TO RELATED APPLICATIONS

This application claims the benefit of U.S. Provisional Patent Application No. 61/255,354, filed Oct. 27, 2009, which is incorporated by reference herein in its entirety.

BACKGROUND

1. Field

Embodiments of the present invention relate to ultrasound (acoustic) data transmission systems, in particular data transmission over wide-band acoustic channels with frequency-dependent multi-path propagation. More specifically, embodiments of the invention relate to data transmission through a wide-band acoustic channel inside a human body.

2. Background

It is well known that a data rate is conventionally proportional to a communication channel bandwidth. For typical acoustic transducers, the frequency bandwidth is about 20% of a carrier. So, for a carrier around 2 MHz, the bandwidth is equal to about 0.4 MHz. This bandwidth allows the system to provide about 800 kbit/s bit rate at the simplest differential quadrature phase-shift keying (DQPSK) modulation scheme with non-coherent signal processing, and about 1600 kbit/s at the very complex 16-quadrature amplitude modulation (QAM) modulation scheme with coherent signal processing.

Image transmission from a capsule inside a human body to an outside receiver requires a very high bit rate exceeding the above-mentioned numbers. Besides, that very high bit rate must be provided at the simplest modulation scheme in the capsule transmitter with minimum power consumption. Therefore, increasing the bit rate is one of the most important and complex tasks of the intra-body acoustic communication technology.

BRIEF SUMMARY

Embodiments of this invention involve increasing the bit rate in the acoustic channel by utilizing the entire ultrasound spectrum available for data transmission.

The available ultrasound spectrum, also referred to herein as the wide-band ultrasound channel, may be divided into several frequency separated sub-channels with utilization different modulation schemes in the sub-channels depending on parameters of both multi-path propagation and signal attenuation in each sub-channel.

According to an embodiment of the present invention, an acoustic data transmitter includes a data buffer configured to accumulate data, a data splitter configured to split the accumulated data in to a plurality of data streams, a plurality of modulators configured to generate a plurality of modulated data signals, each modulator configured to modulate a respective data stream into a data signal according to a respective frequency band and modulation scheme, and a wide-band acoustic transducer configured to generate a wide-band acoustic signal from the plurality of modulated data signals to be propagated over an acoustic channel.

According to an embodiment of the present invention, an acoustic data receiver, includes a wide-band acoustic transducer configured to receive a wide-band acoustic signal and transform the wide-band acoustic signal into a plurality of frequency-divided sub-band signals, a plurality of demodulators configured to generate a plurality of data streams, each demodulator configured to demodulate a respective sub-band signal into a data stream according to a respective frequency band and demodulation scheme, and a data combiner configured to combine the plurality of data streams into a high bit rate data stream.

According to an embodiment of the present invention, a method of modulating acoustic data includes dividing a wide-band acoustic data channel into N sub-bands, wherein the first sub-band corresponds to a maximum echo delay and a minimum signal attenuation and the Nth sub-band corresponds to a minimum echo delay and a maximum signal attenuation, such that echo delay decreases and signal attenuation increases as sub-bands increase in frequency from the first sub-band to the Nth sub-band, modulating data for each sub-band using an acoustic modulation scheme that is different from modulation schemes used in other sub-bands, and combining the modulated data from each sub-band into a wide-band acoustic data signal.

Further features and advantages of the invention, as well as the structure and operation of various embodiments of the invention, are described in detail below with reference to the accompanying drawings. Note that the Summary section may set forth one or more, but not all exemplary embodiments of the present invention as contemplated by the inventor(s).

BRIEF DESCRIPTION OF THE DRAWINGS/FIGURES

The accompanying drawings illustrate the present invention and, together with the description, further serve to explain the principles of the invention and to enable one skilled in the pertinent art to make and use the invention.

DETAILED DESCRIPTION

Embodiments of this invention involve increasing the bit rate in the acoustic channel by means of utilization of the entire ultrasound spectrum available for data transmission.

The lower bound of this spectrum is about 100 kHz, and the upper bound depends on maximum acceptable attenuation. Attenuation of ultrasound waves in the body depends considerably on both carrier frequency and propagation distance. According to experimental results obtained by Innurvation, Inc. of Columbia, Md., average attenuation A (dB) of an ultrasound signal inside the human body can be approximated as follows:

$$A \approx 0.75 LF \text{ dB}, \qquad (\text{Eq. 1})$$

where L (cm) is the distance between a capsule transmitter inside a human body and an external receiver on the surface of the human body, and F (MHz) is the carrier frequency. An exemplary acoustic transmitter capsule in which embodiments of the present invention may be used is described in U.S. Pat. Appl. Publ. No. 2008/0146871, which is incorporated by reference herein in its entirety. Such a capsule may emit acoustic signals to be detected by an external receiver, such as a patch receiver located on a surface of a human body.

If a maximum distance between the capsule and the receiver $L_{max}=20$ cm, then the minimum attenuation at $F_{min}=0.1$ MHz is equal to about $A_{min}=1.5$ dB. On the other hand, if maximum acceptable attenuation within the spectrum is about $A_{max}=30$ dB, then the upper bound of the spectrum is equal to about $F_{max}=A_{max}/0.75L_{max}=30/0.75*20=2$ MHz.

So, the frequency band of approximately 0.1-2.0 MHz can be used for data transmission in the intra-body acoustic communication channel. This channel will be referred to herein as the wide-band ultrasound channel.

There are well-known difficulties in utilization of wide-band channels as a whole for high data rate transmission by means of a single carrier with various modulation techniques.

The first obstacle can be described as follows: a signal bandwidth cannot exceed its carrier frequency (otherwise, each symbol will contain less than one period of the carrier). For example, at a carrier frequency of 1 MHz, the symbol duration should not be less than 1 us (one period of the carrier), which corresponds to a signal with a bandwidth of about 1 MHz. In the considered case, the channel bandwidth is close to 2 MHz, but the corresponding signal cannot be transmitted by means of the 2 MHz carrier as the upper-sideband of this signal may be severely attenuated.

The second obstacle is related to multi-path signal propagation in the intra-body acoustic channel, caused by reflections of acoustic waves from different objects (e.g., tissues) inside the body, surface areas, and surface boundaries. Superposition of the main shortest-path ray and numerous echo rays causes both inter-symbol interference and signal fading at the receiver. An embodiment of a wide-band ultrasound channel includes considerable changing of multi-path propagation conditions in the frequency domain—the more frequency, the less influence of echo signals. This phenomenon can be explained as follows.

Two propagation paths (rays) from the transmitter to the receiver are considered with path distances $L_1$ and $L_2$, where $L_2 > L_1$. Attenuations of these rays are equal to $A_1 = 0.75 L_1 F$ dB and $A_2 = 0.75 L_2 F$ dB, correspondingly. If the first ray can be considered to be the useful signal, and the second ray to be the interference, then the signal-to-interference ratio (SIR) at the input of the receiver is equal to $$\text{SIR} = -A_1 + A_2 = 0.75(L_2 - L_1)F \text{ dB}. \qquad (\text{Eq. 2})$$

Eq. 2 shows that with increasing the acoustic carrier frequency, the influence of the delayed ray decreases. For example, at F=1 MHz and $(L_2-L_1)$=10 cm, the SIR=7.5 dB, but at F=2 MHz and the same distance difference, the SIR=15 dB. Simulation of multipath signal processing shows that at the bit error rate BER=0.001, the influence of any delayed ray can be neglected if it is less than the main ray by at least 12 dB. Using this assumption and based on Eq. 2, it can be concluded that, at F=2 MHz, any acoustic ray with a delay of more than 8 cm relative to the main ray can be neglected.

The above consideration shows that the wide-band ultrasound intra-body channel can be conditionally divided into three main frequency areas: a multi-path area with a carrier frequency below 1.0 MHz, a single-path area with a carrier frequency above 1.5 MHz, and a transient area between 1.0 MHz and 1.5 MHz with progressive transition from the multi-path channel to the single-path channel.

Both of the difficulties described above regarding utilization of wide-band channels as a whole for high data rate transmission—large bandwidth of the signal compared with possible carrier frequency, and frequency-dependable multi-path propagation parameters—can be overcome by embodiments of the invention.

Embodiments of the present invention are based on dividing the wide-band ultrasound channel into several frequency separated sub-channels with utilization different modulation schemes in the sub-channels depending on parameters of both multi-path propagation and signal attenuation in each sub-channel.

Figure 1:
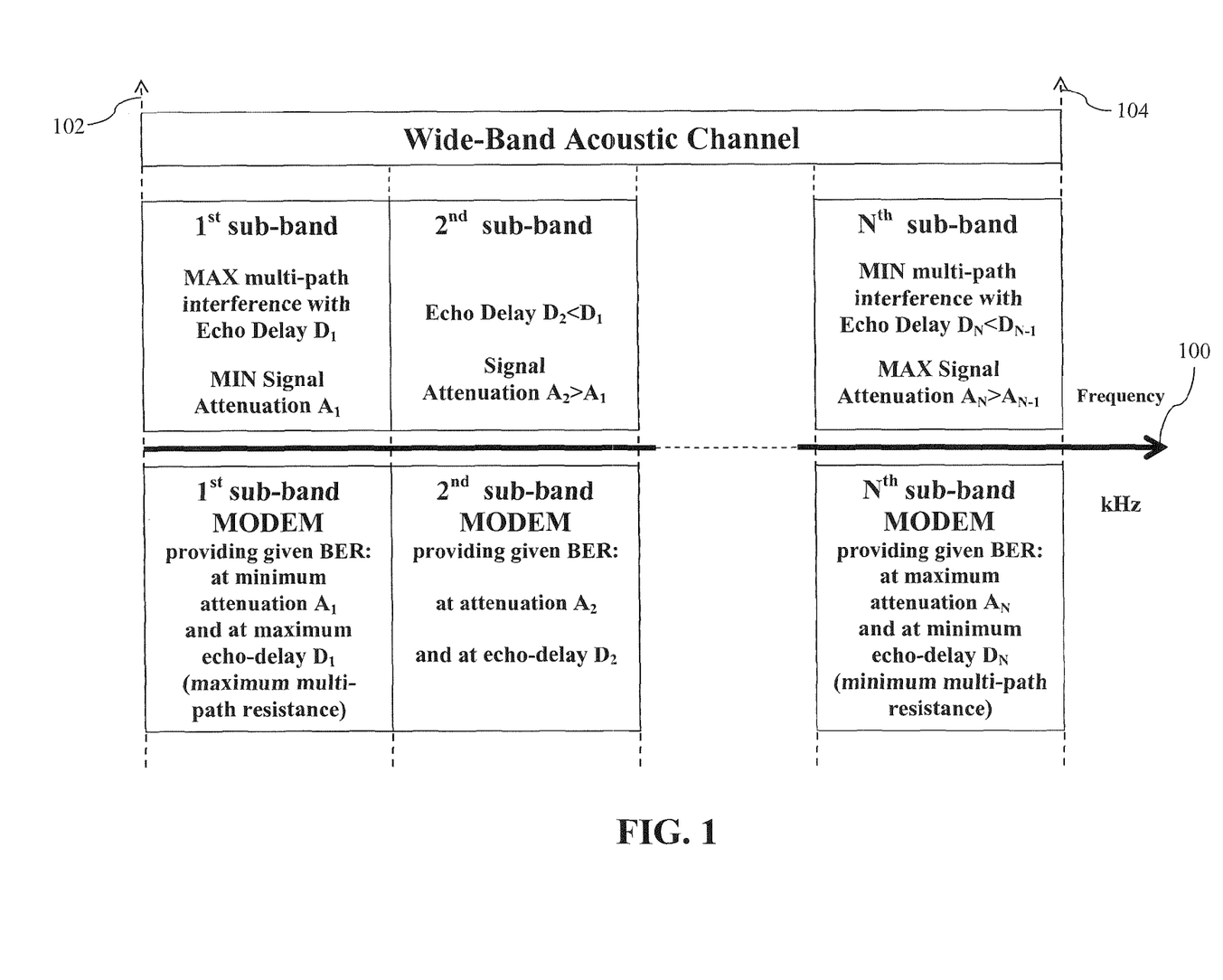
FIG. 1 is schematic explanation of a method of wide-band acoustic communication, according to an embodiment of the invention.

FIG. 1 provides schematic illustration of a method of wide-band acoustic communication, according to an embodiment of the invention. Frequency axis 100 indicates a wide-band acoustic channel in the frequency domain. The channel as a whole occupies the frequency band from the lower boundary 102 to the upper boundary 104—the space labeled "Wide-Band Acoustic Channel" in FIG. 1.

According to an embodiment of the method, the wide-band channel is divided into N sub-bands, indicated in FIG. 1 by squares above frequency axis 100. As one can see, N sub-band modems, indicated in FIG. 1 by squares below the frequency axis, are used in the corresponding sub-bands.

The $1^{st}$ sub-band, occupying the lower frequencies, corresponds to the most severe multi-path interference with maximum echo delay $D_1$, but, on the other hand, it is characterized by minimum signal attenuation $A_1$. So, the $1^{st}$ sub-band modem provides the required BER at minimum signal attenuation (maximum SNR) and at maximum echo-delay. In other words, the $1^{st}$ sub-band modem has maximum resistance to multi-path propagation and minimum resistance to the noise. For example, a multi-carrier modem uses in this case maximum sub-carriers with maximum guard-interval for mitigating inter-symbol interference, and, at the same time the modem uses maximum number of signal positions to maximize bit rate at the lowest signal attenuation.

When moving from one sub-band to another sub-band from left to right in FIG. 1, the echo-delay decreases and the signal attenuation increases (SNR decreases). Correspondingly, requirements for modems are changed.

The $2^{nd}$ sub-band occupies a frequency area with the echo delay $D_2 < D_1$, but, on the other hand, it is characterized by the signal attenuation $A_2 > A_1$. The $2^{nd}$ sub-band modem provides adequate resistance to multi-path propagation and to the noise. For example, the multi-carrier modem uses in this case a lesser guard-interval than the $1^{st}$ sub-band modem, and it provides the required BER at SNR, which is lesser than the SNR in the $1^{st}$ sub-band modem.

The $N^{th}$ sub-band, occupying the upper frequencies of the wide-band acoustic spectrum, corresponds to the practically single-path propagation with minimum echo delay $D_N$, but, on the other hand, it is characterized by maximum signal attenuation $A_N$. So, the $N^{th}$ sub-band modem provides the required BER at maximum signal attenuation (minimum SNR) and at minimum echo-delay. In other words, the $N^{th}$ sub-band modem has minimum resistance to multi-path propagation and maximum resistance to the noise. For example, the single-carrier modem with simple QPSK modulation can be used in this case.

Figure 2:
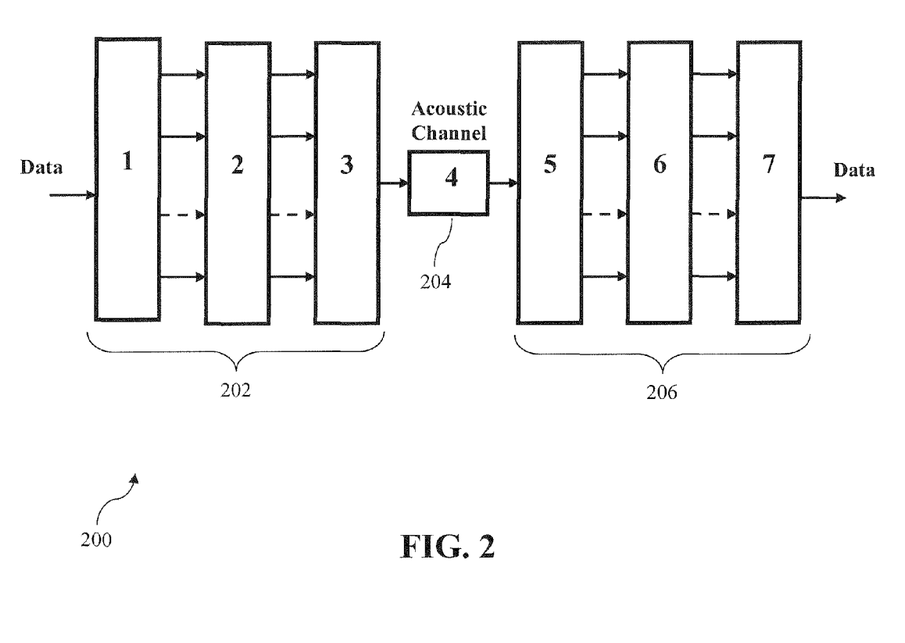
FIG. 2 is a general block diagram of a wide-band acoustic communication system, according to an embodiment of the invention.

FIG. 2 shows a high level general block diagram of a wide-band acoustic communication system 200, including a transmitter 202, an acoustic channel 204, and a receiver 206, according to an embodiment of the invention. In an embodiment, a data stream at transmitter 202, for example, a digitized image, is divided into several data streams in block 1. Generally, block 1 includes a data buffer and a splitter, which may be synchronized from a common sync-generator. Block 1 outputs data streams to block 2, which includes a set of sub-band modulators, each having a unique modulation scheme. Each sub-band scheme transforms its individual data stream into a complex modulated signal within an individual frequency sub-band, separated from other sub-bands. The modulated signal can contain one or several sub-carriers, depending on characteristics of that particular ultrasound frequency sub-band. Parallel signals from block 2 are fed to the block 3, a wide-band acoustic transducer. Block 3 can include, for example, several narrow-band selective acoustic transducers. Block 3 generates a wide-band ultrasound signal which is propagated over acoustic channel 204, illustrated as block 4. At receiver 206, block 5, an acoustic transducer, transforms the wide-band acoustic signal into a parallel set of sub-band signals, corresponding to frequency sub-band division in the transmitter. Block 5 can include frequency selective acoustic transducer or pass-band selective filters or both. Block 5 outputs parallel frequency separated signals to block 6, which is a set of sub-band demodulators, each having a demodulation scheme to correspond with a modulation scheme used in the transmitter 202. Each sub-band demodulation scheme transforms the sub-band signal into a data stream. All individual data streams from outputs of block 6 are combined into a single high bit rate data stream in block 7. Block 7 may include, for example, a parallel-sequential data buffer, which may be synchronized from a receiver sync-generator.

Figure 3:
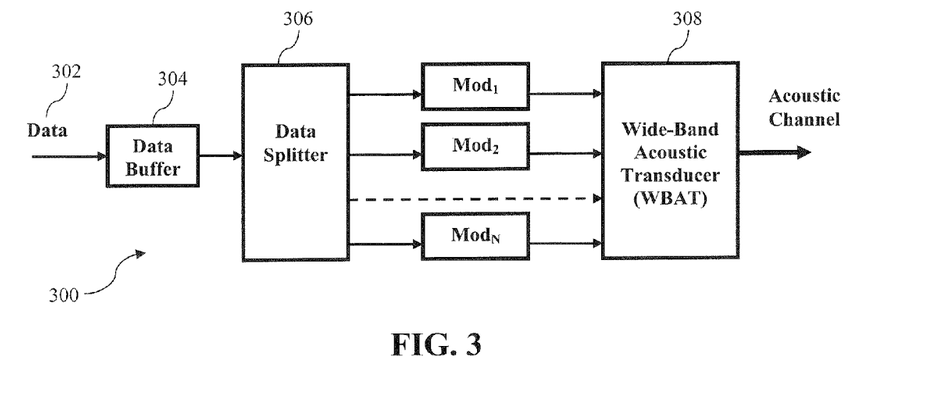
FIG. 3 is a general block diagram of a wide-band acoustic transmitter, according to an embodiment of the invention.

FIG. 3 shows a general block diagram of a wide-band acoustic transmitter 300 according to an embodiment of the invention, which can be a capsule transmitter inside a human body.

Data 302 from a capsule scanner or any other image capture device is first accumulated in a data buffer 304, and then is split into N streams for N modulation schemes $MOD_n$, where n=1 . . . N, by data splitter 306. Each modulation scheme $MOD_n$ provides specific transformation of the input data stream into the modulated signal within a separate frequency band. All individual modulation schemes output their signals to the input of a wide-band acoustic transducer (WBAT) 308. Wide-band acoustic transducer 308 can be implemented in various ways. For example, it may be a proper combination of narrow-band frequency selective transducers with matched frequency characteristics. In any case, wide-band transducer 308 provides transformation of a superposition of the input signals $MOD_n$ into the wide-band acoustic signal, which is finally transmitted through an acoustic channel, for example, through an intra-body acoustic channel.

Figure 4:
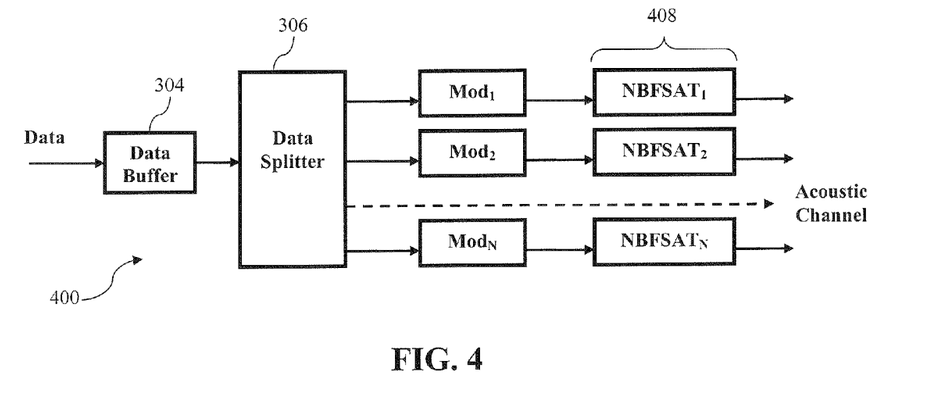
FIG. 4 is a block diagram of a wide-band acoustic transmitter, based on a set of narrow-band frequency selective acoustic transducers, according to an embodiment of the invention.

FIG. 4 illustrates a block diagram of a wide-band acoustic transmitter 400 according to an embodiment of the invention, based on a set of narrow-band frequency selective acoustic transducers (NBFSAT) 408. In this case, each modulation scheme outputs the modulated signal $MOD_n$ to its individual transducer 408, working within some separate and comparatively narrow frequency band—narrow-band frequency selective acoustic transducer (NBFSAT) 408.

Figure 5:
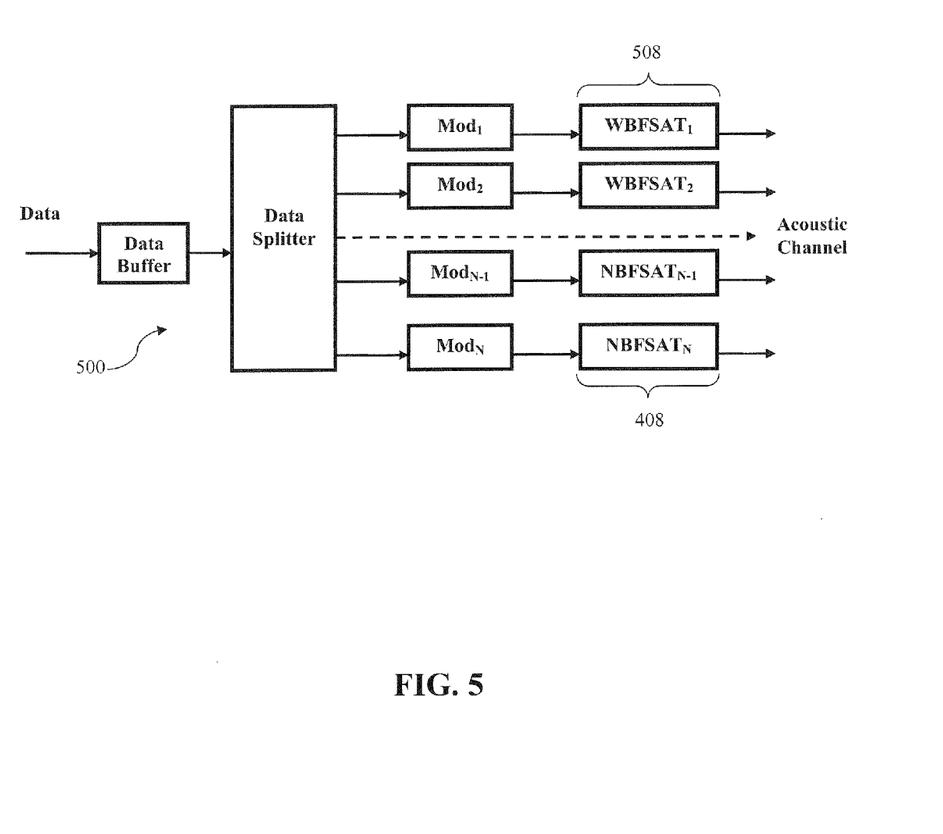
FIG. 5 is a block diagram of a wide-band acoustic transmitter, based on a combination of wide-band frequency selective transducers and narrow-band frequency selective acoustic transducers, according to an embodiment of the invention.

FIG. 5 illustrates another block diagram of a wide-band acoustic transmitter 500 according to an embodiment of the invention, based on a combination of wide-band frequency selective transducers (WBFSAT) 508 and narrow-band frequency selective acoustic transducers (NBFSAT) 408. In this case, the scheme contains both wide-band and narrow band transducers. According to an embodiment, in the lower part of the acoustic spectrum, wide-band frequency selective transducers 508 are used, based on, for example, combining narrow-band frequency selective transducers 408 with matched frequency characteristics, and in the upper part of the acoustic spectrum, narrow-band frequency selective transducers 408 are used. This mixed structure allows the transmitter to divide the utilized acoustic spectrum unto approximately equal parts in the frequency domain and, at the same time, to minimize a number of subcarriers.

Figure 6:
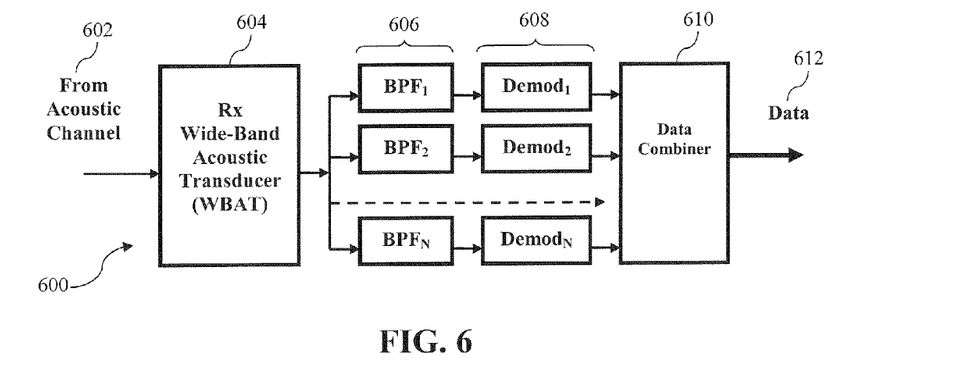
FIG. 6 is a general block diagram of a wide-band acoustic receiver, according to an embodiment of the invention.
Figure 7:
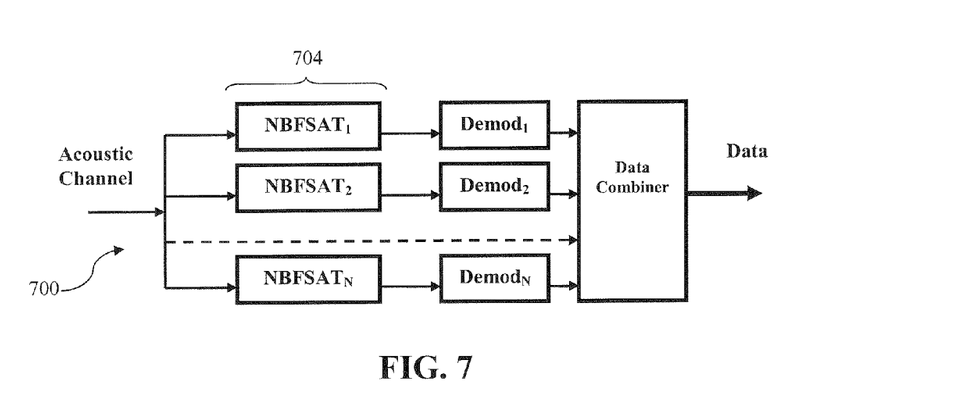
FIG. 7 is a block diagram of a wide-band acoustic receiver, based on a set of narrow-band frequency selective acoustic transducers, according to an embodiment of the invention.
Figure 8:
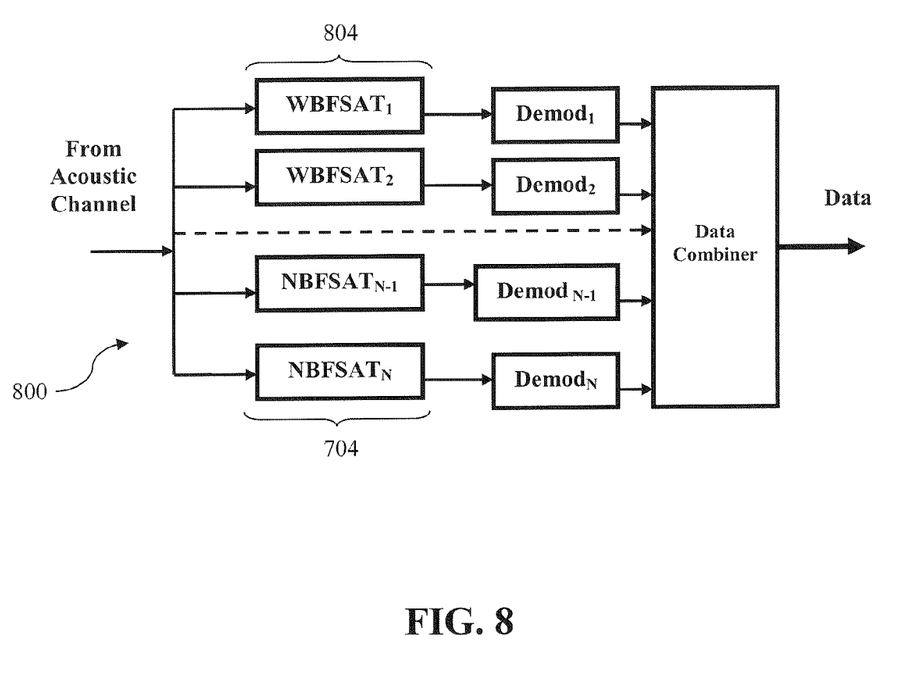
FIG. 8 is a block diagram of a wide-band acoustic receiver, based on a combination of wide-band frequency selective transducers and narrow-band frequency selective acoustic transducers, according to an embodiment of the invention.

Schemes of wide-band acoustic receivers, such as those shown in FIG. 6-8, may be mirror reflections of the above wide-band acoustic transmitters.

FIG. 6 shows a general block diagram of a wide-band acoustic receiver 600 according to an embodiment of the invention, which can be, for example, a patch receiver outside a human body.

A received ultrasound signal 602 from an acoustic channel is first transformed into electrical signal by means of a wide-band acoustic transducer (WBAT) 604. The WBAT output signal is then filtrated by a set of parallel band-pass filters (BPF) 606. Each partial signal from the output of the BPF is demodulated by a respective demodulator (Demod) 608, which corresponds to the modulation scheme utilized in the corresponding branch of the wide-band transmitter. Finally, a data combiner 610 combines data streams from outputs of demodulators 608 into a common data stream 612.

FIG. 7 illustrates a block diagram of a wide-band acoustic receiver 700 according to an embodiment of the invention, based on a set of narrow-band frequency selective acoustic transducers (NBFSAT) 704. In this case, the NBFSATs 704 combine functions of receiving ultrasound transducers and band-pass filters.

FIG. 8 illustrates a block diagram of a wide-band acoustic receiver 800, according to an embodiment of the invention, based on the combination of wide-band frequency selective transducers (WBFSAT) 804 and narrow-band frequency selective acoustic transducers (NBFSAT) 704. As well as in the previous case, in this scheme WBFSATs 804 and NBFSATs 704 play role of both receiving ultrasound transducers and band-pass filters.

Detailed schemes of the above-described wide-band acoustic transmitters and receivers depend on both a method of partition of the ultrasound spectrum and the modulation scheme inside each part of the spectrum.

Examples of spectrum partitioning and modulation schemes are now described, focusing on use with an intra-body acoustic communication channel.

Figure 9A:
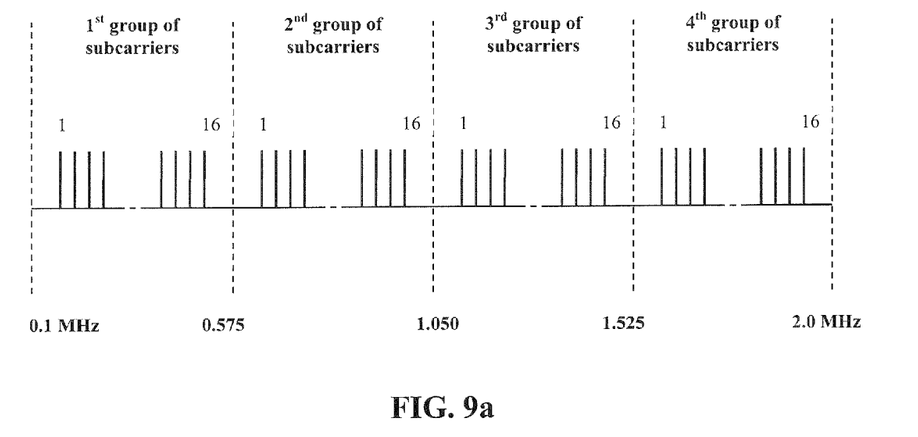
FIG. 9a illustrates a wide-band ultrasound signal with uniformly distributed subcarriers in the frequency area from 100 kHz to 2.0 MHz, according to an embodiment of the invention.

FIG. 9a shows a wide-band ultrasound signal with uniformly distributed subcarriers in the frequency area from 100 kHz to 2.0 MHz, according to an embodiment of the invention. The signal contains 64 subcarriers combined into 4 groups with 16 subcarriers in each group. Subcarriers within each group are separated by 25 kHz, and the groups are separated by 100 kHz. This allows a receiver to reliably select each group of subcarriers and provide proper symbol synchronization (see below).

It should be noted that subcarriers in the signal in FIG. 9a are orthogonal functions because they are harmonics of the 25 kHz oscillation. So, this multicarrier signal can be considered as a 64-carrier OFDM (Orthogonal Frequency Division Multiplexing) signal. However, in contrast to a conventional OFDM signal and according to the embodiment of this invention, the guard interval and the symbol duration of signals can be different in all subcarrier groups because of differences of multi-path intervals in lower and upper parts of the ultrasound spectrum.

The symbol interval in OFDM systems includes two parts: a guard interval $T_g$ and an active interval $T_a$ (the last one is also called the interval of orthogonality). The active interval is strongly determined as inverse proportional to the subcarrier separation interval $\Delta f$, namely: $T_a = k/\Delta f$, where k is an integer. If in the considered example $\Delta f = 25$ kHz, then $T_a = 40$ us at k=1. It should be noted that this value of $T_a$ is used in all 4 groups of subcarriers in the wide-band signal in FIG. 9a.

In contrast to the active interval, the guard interval $T_g$ can be different for different groups depending on multi-path interval within the corresponding parts of the ultrasound spectrum. Taking into account realistic multi-path propagation in the intra-body acoustic channel, the following values of the guard interval can be considered in the groups of subcarriers: $T_g=100$ us for the $1^{st}$ group (0.1-0.575 MHz), $T_g=60$ us for the $2^{nd}$ group (0.575-1.050 MHz), $T_g=20$ us for the 3-rd group (1.050-1.525 MHz), $T_g=5$ us for the $4^{th}$ group (1.525-2.0 MHz).

The total bit rate can be calculated as follows:

$$B_T = \Sigma N_i * \log M_i/(T_g+T_a), \quad\quad (Eq. 3)$$

where $N_i$ corresponds to a number of subcarriers in the i-th group, and $M_i$ corresponds to a number of positions in the modulated signal in the i-th subcarrier group.

For $N_i=16$ and M=4 (DQPSK modulation), Eq. 3 provides:

$$B_T(QPSK) = 10^3 \left( \begin{array}{c} 16*2/140 + 16*2/100 + \\ 16*2/60 + 16*2/45 \end{array} \right) \quad (Eq. 4a)$$
$$== 228 + 320 + 533 + 711$$
$$= 1792 \text{ kbit/s}$$

Taking into account that signals in the $1^{st}$ and $2^{nd}$ groups of subcarriers have lesser attenuation than signals in the $3^{rd}$ and $4^{th}$ groups, it is possible to use M=8 (8-DPSK modulation scheme) in the $1^{st}$ and $2^{nd}$ groups. As a result, Eq. 3 provides:

$$B_T(DQPSK + 8-DPSK) = 10^3 \left( \begin{array}{c} 16*3/140 + 16*3/100 + \\ 16*2/60 + 16*2/45 \end{array} \right) \quad (4b)$$
$$= 343 + 480 + 533 + 711$$
$$= 2067 \text{ kbit/s}.$$

So, as one can see from Eq. 4, a method of data transmission through the wide-band acoustic channel according to an embodiment provides about 2 Mbit/s bit rate using comparatively simple modulation schemes—DQPSK and 8-DPSK allowing utilization of non-coherent signal processing in the receiver.

Figure 10:
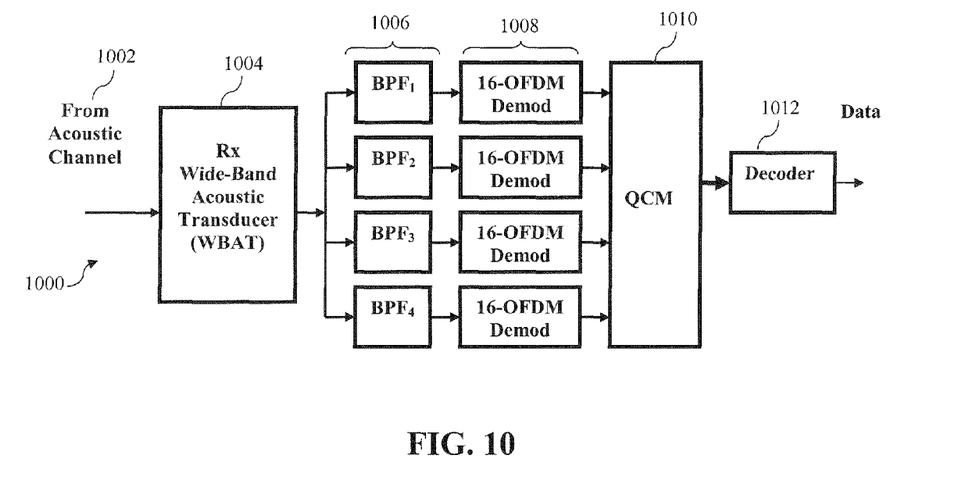
FIG. 10 is a block diagram of a wide-band acoustic receiver for signals with uniformly distributed subcarriers, according to an embodiment of the invention.

FIG. 10 shows a general block diagram of a wide-band acoustic receiver 1000 according to an embodiment of the invention for signals in FIG. 9a with uniformly distributed subcarriers. A received ultrasound signal 1002 from an acoustic channel is first transformed into an electrical signal by means of a wide-band acoustic transducer (Rx-WBAT) 1004. The WBAT output signal is then filtrated by a set of parallel band-pass filters (BPF) 1006. Each partial signal from the output of the BPF is demodulated by an individual 16-subcarrier OFDM demodulator 1008. Reference signals of each 16-OFDM demodulator are replicas of the corresponding subcarriers from one of 4 groups of subcarriers (see FIG. 9a). It should be noted that the 16-OFDM demodulator can be implemented in various manners, for example, as the Fast Fourier Transformer (FFT) or as a set of 16 quadrature correlators, and both coherent and non-coherent signal processing can be used. In any case, the output of each 16-OFDM provides the output signal in form of 16 complex numbers, corresponding to quadrature correlation coefficients for 16 subcarriers. These 16 complex numbers are saved in operative memory QCM (Quadrature Correlation Memory) 1010. Decoder 1012 transforms two complex numbers, corresponding to current and previous symbols of each subcarrier into the transmitted bit combination, containing 2 bits in the case of DQPSK and 3 bits in the case of 8-DPSK modulation schemes. During symbol duration, which may be different for different branches of the receiver, decoder 1012 may provide decoding output signals of all 64 subcarriers from 4 branches.

Figure 9B:
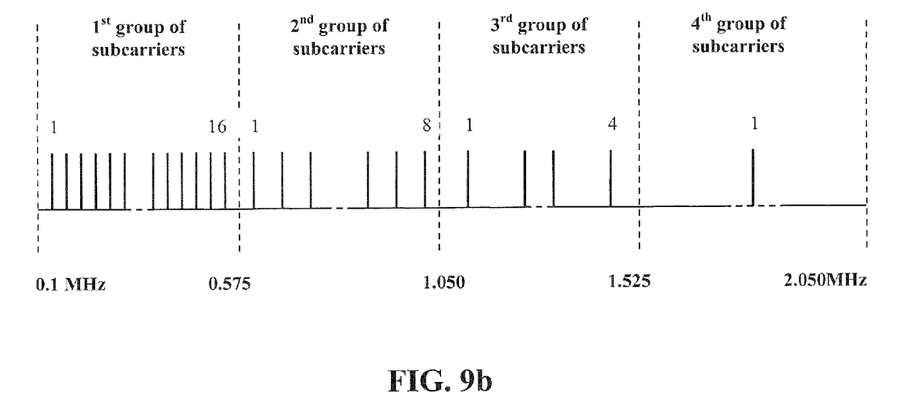
FIG. 9b illustrates a wide-band ultrasound signal with non-uniformly distributed subcarriers in frequency domain, according to an embodiment of the invention.

FIG. 9b shows another example of the wide-band ultrasound signal with nonuniformly distributed subcarriers in the frequency area from 100 kHz to 2.05 MHz, according to an embodiment of the invention. The wide-band signal is also combined into 4 groups, but numbers of subcarriers in each group are not equal. The $1^{st}$ group contains 16 subcarriers as well as in the signal in FIG. 9a, the $2^{nd}$ group contains 8 subcarriers, the $3^{rd}$ group contains 4 carriers, and the 4th group contains only one carrier. In other words, the number of subcarriers increases with increasing influence of multi-path propagation.

Modulation schemes in different groups are also different. The 4th group is subjected to maximum attenuation and minimum multi-path interference. Therefore, it is reasonable to use in this group the simplest single-carrier DQPSK modulation scheme with symbol duration $T=T_g+T_a=2$ us, which provides a bit rate $B_4=1.0$ Mbit/s The $3^{rd}$ group is subjected to more multi-path interference, but with lesser attenuation. Therefore, it is reasonable to use in this group 4 carriers with 125 kHz separation, e.g. with $T_a=8$ us, and with the guard interval $T_g=12$ us. Using 8-DPSK, the bit rate of this group is equal to $B_3=4*3/20=600$ kbit/s.

The $2^{nd}$ group is subjected to considerable multi-path interference, but with little attenuation. Therefore, it is reasonable to use in this group 8 carriers with 55 kHz separation, e.g. with $T_a=18$ us, and with the guard interval $T_g=32$ us. Using 8-DPSK, the bit rate of this group is equal to $B_2=8*3/50=480$ kbit/s.

The $1^{st}$ group is subjected to maximum multi-path interference, but with minimum attenuation. Therefore, it is reasonable to use in this group 16 subcarriers with 25 kHz separation, e.g. with $T_a=40$ us, and with the guard interval $T_g=100$ us. Because of negligible attenuation, it is possible to use 16-QAM modulation scheme, which provides bit rate $B_1=16*4/140=457$ kbit/s.

The total bit rate for this wide-band acoustic system with nonuniformly distributed subcarriers may be equal to 1000+600+480+457=2537 kbit/s.

Figure 11:
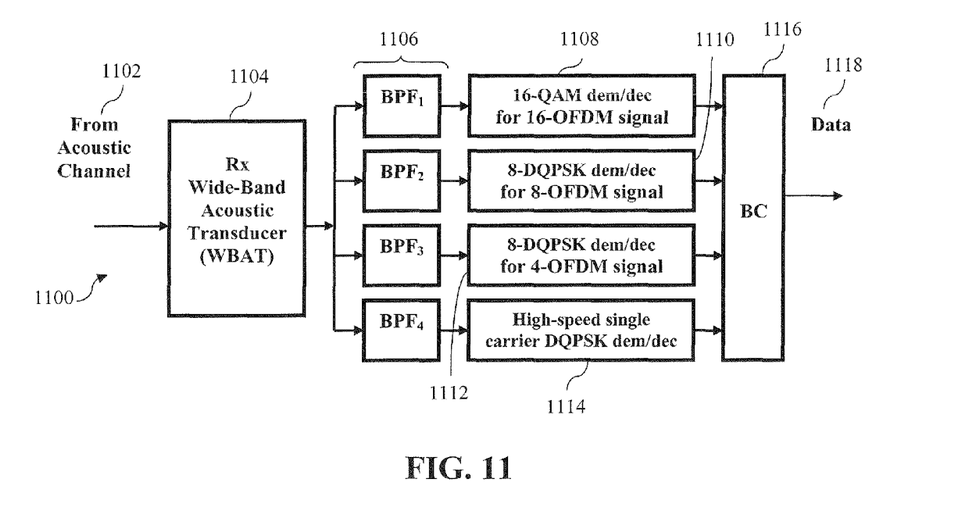
FIG. 11 is a block diagram of a wide-band acoustic receiver for signals with nonuniformly distributed subcarriers, according to an embodiment of the invention.

FIG. 11 shows a general block diagram of a wide-band acoustic receiver according to an embodiment of the invention for signals in FIG. 9b with nonuniformly distributed subcarriers. The received ultrasound signal 1102 from the acoustic channel is first transformed into an electrical signal by means of wide-band acoustic transducer (Rx-WBAT) 1104. The WBAT output signal is then filtrated by a set of parallel band-pass filters (BPF) 1106. Each partial signal from the output of the BPF is processed by an individual demodulator/decoder (dem/dec) 1108. Reference signals of each dem/dec are replicas of the corresponding subcarriers from one of 4 groups of subcarriers (see FIG. 9b). In this example, an individual dem/dec can be implemented as follows.

A demodulator/decoder of the $1^{st}$ branch of the wide-band receiver may be the 16-QAM dem/dec 1108 for the 16-OFDM signal. It can be implemented as the Fast Fourier Transformer (FFT) or as a set of 16 quadrature correlators. The coherent signal processing may be used in this particular case. The output of dem/dec 1108 provides 16 of 4-bits combinations per each OFDM symbol, i.e. 8 bytes of information per the 16-carrier symbol.

A demodulator/decoder of the $2^{nd}$ branch of the wide-band receiver may be the 8-DPSK dem/dec 1110 for the 8-OFDM signal. It can be implemented as a set of 8 quadrature correlators. Both coherent and non-coherent signal processing can be used in this particular case. The output of dem/dec 1110 provides 8 of 3-bits combinations per each OFDM symbol, i.e. 3 bytes of information per the 8-carrier symbol.

A demodulator/decoder of the $3^{rd}$ branch of the wide-band receiver may be the 8-DPSK dem/dec 1112 for the 4-OFDM signal. It can be implemented as a set of 4 quadrature correlators. Both coherent and non-coherent signal processing can be used in this particular case. The output of dem/dec 1112 provides 4 of 3-bits combinations per each OFDM symbol, i.e. 1.5 bytes of information per the 4-cagier symbol.

A demodulator/decoder of the 4th branch of the wide-band receiver may be the DQPSK single carrier dem/dec 1114, providing high bit rate transmission with very short symbols. It can be implemented as the non-coherent DQPSK dem/dec, based on conventional quadrature demodulator. The output of dem/dec 1114 provides a 2-bit combination per each short symbol.

Outputs of the dem/decs are input to a bit combiner 1116, to generate a single, high bit rate data stream 1118.

Exemplary modulation schemes that may be used in or in conjunction with the present invention are described in U.S. Pat. Appl. Publ. No. 2008/0161660, U.S. Pat. Appl. Publ. No. 2008/0112885, and U.S. Pat. Appl. Publ. No. 2008/0114224, each of which is incorporated by reference herein in its entirety. An exemplary acoustic transmitter in which embodiments of the present invention may be used is described in U.S. Pat. Appl. Publ. No. 2008/0146871, which is incorporated by reference herein in its entirety.

The present specification discloses one or more embodiments that incorporate the features of the invention. The disclosed embodiment(s) merely exemplify the invention. The scope of the invention is not limited to the disclosed embodiment(s). References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. The example embodiments described herein are provided for illustrative purposes, and are not limiting. Further structural and operational embodiments, including modifications/alterations, will become apparent to persons skilled in the relevant art(s) from the teachings herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An acoustic data transmitter, comprising:
   a data buffer configured to accumulate data;
   a data splitter configured to split the accumulated data into a plurality of data streams occupying corresponding frequency bands;
   a plurality of modulators configured to modulate a respective data stream from among the plurality of data streams in accordance with a modulation scheme associated with a respective frequency band to generate a plurality of modulated data signals; and
   a wide-band acoustic transducer configured to generate a wide-band acoustic signal incorporating each of the plurality of modulated data signals to be propagated over an acoustic channel at the same time;
   wherein the wideband acoustic signal comprises a plurality of sub-bands corresponding to the plurality of data streams modulated with a plurality of modulation schemes.

2. The acoustic data transmitter of claim 1, wherein the wide-band acoustic transducer comprises:
   a plurality of individual acoustic transducers, each individual acoustic transducer from among the plurality of individual acoustic transducers being configured to generate an acoustic signal based on a respective one of the plurality of modulated data streams.

3. The acoustic data transmitter of claim 2, wherein the plurality of acoustic transducers includes a plurality of wide-band frequency selective acoustic transducers, a plurality of narrow-band frequency selective acoustic transducers, or a combination of wide-band frequency selective acoustic transducers and narrow-band frequency selective acoustic transducers.

4. The acoustic data transmitter of claim 1, wherein the acoustic channel includes living tissue.

5. The acoustic data transmitter of claim 1, further comprising:
an ingestible capsule housing surrounding the data buffer, the data splitter, and the acoustic transducer.

6. The acoustic data transmitter of claim 1, wherein the plurality of modulators is further configured to generate the plurality of modulated data signals depending on parameters related to multi-path propagation and signal attenuation in the respective frequency band.

7. The acoustic data transmitter of claim 1, wherein the plurality of modulators is further configured to modulate a respective data stream at a lower frequency band using more subcarriers than a respective data stream at a higher frequency band.

8. The acoustic data transmitter of claim 1, wherein the modulation scheme includes differential quadrature phase-shift keying or quadrature amplitude modulation.

9. An acoustic data receiver, comprising:
a wide-band acoustic transducer configured to receive a wide-band acoustic signal and to transform the wide-band acoustic signal into a plurality of frequency-divided sub-band signals;
a plurality of demodulators configured to generate a plurality of data streams, each demodulator from among the plurality of demodulators being configured to demodulate a respective sub-band signal into a data stream according to a respective frequency band and demodulation scheme; and
a data combiner configured to combine the plurality of data streams into a data stream;
wherein the plurality of frequency-divided sub-band signals are modulated with a plurality of modulation schemes.

10. The acoustic data receiver of claim 9, wherein the wide-band acoustic transducer comprises:
a plurality of individual acoustic transducers, each individual acoustic transducer from among the plurality of individual acoustic transducers being configured to generate an acoustic signal based on a respective one of the plurality of sub-band signals.

11. The acoustic data receiver of claim 10, wherein the plurality of acoustic transducers includes a plurality of wide-band frequency selective acoustic transducers, plurality of narrow-band frequency selective acoustic transducers, or a combination of wide-band frequency selective acoustic transducers and narrow-band frequency selective acoustic transducers.

12. The acoustic data receiver of claim 9, wherein the plurality of demodulators is further configured to demodulate a respective data stream at a lower sub-band using more subcarriers than a respective data stream at a higher sub-band.

13. The acoustic data receiver of claim 9, wherein the demodulation scheme includes differential quadrature phase-shift keying or quadrature amplitude demodulation.

14. A method of modulating acoustic data, comprising:
dividing a wide-band acoustic data channel into N sub-bands, wherein the first sub-band corresponds to a maximum echo delay and a minimum signal attenuation and the Nth sub-band corresponds to a minimum echo delay and a maximum signal attenuation, such that echo delay decreases and signal attenuation increases as sub-bands increase in frequency from the first sub-band to the Nth sub-band; and
modulating data within each sub-band from among the N sub-bands using an acoustic modulation scheme that is different from modulation schemes used in other sub-bands; and
combining the modulated data from each sub-band from among the N sub-bands into a wide-band acoustic data signal;
wherein the sub-bands are modulated with a plurality of modulation schemes.

15. The method of claim 14, further comprising:
transmitting the wide-band acoustic data signal via a plurality of transducers.

16. The method of claim 14, wherein the transmitting comprises;
transmitting the wide-band acoustic data signal via a combination of wide-band frequency selective transducers and narrow-band frequency selective acoustic transducers.

17. The method of claim 14, wherein the modulating comprises:
modulating data in the first sub-band and the Nth sub-band using a first and a second number of carriers, respectively, the first number of carriers being greater than the second number of carriers.

18. The method of claim 14, wherein the modulating comprises:
modulating data in the first sub-band using quadrature amplitude modulation; and
modulating data in the Nth sub-band using differential quadrature phase-shift keying modulation.

* * * * *